United States Patent [19]

Takamoto et al.

[11] Patent Number: 5,699,153

[45] Date of Patent: Dec. 16, 1997

[54] METHOD AND APPARATUS FOR OPTICAL INSPECTION

[75] Inventors: Kenji Takamoto, Neyagawa; Kanji Nishii, Osaka; Masami Ito, Moriguchi; Atsushi Fukui, Osaka, all of Japan

[73] Assignee: Matsushita Electric Industrial Co., Ltd., Osaka-fu, Japan

[21] Appl. No.: 550,682

[22] Filed: Oct. 31, 1995

[30] Foreign Application Priority Data

Oct. 31, 1994 [JP] Japan ................................. 6-267168

[51] Int. Cl.⁶ .................................................. G01N 21/88
[52] U.S. Cl. .................................................. 356/237
[58] Field of Search ........................... 356/237, 239, 356/430, 431; 250/559.42

[56] References Cited

U.S. PATENT DOCUMENTS

| | | | |
|---|---|---|---|
| 3,574,470 | 4/1971 | Paine et al. | 356/237 |
| 3,976,384 | 8/1976 | Matthews et al. | 356/239 |
| 4,538,909 | 9/1985 | Bible et al. | 356/239 |
| 4,555,179 | 11/1985 | Langerholc et al. | 356/237 |
| 5,137,355 | 8/1992 | Barbour et al. | 356/237 |
| 5,355,213 | 10/1994 | Dotan | 356/239 |
| 5,517,301 | 5/1996 | Davé | 356/239 |

FOREIGN PATENT DOCUMENTS 4-16751  1/1992  Japan .

*Primary Examiner*—F. L. Evans
*Attorney, Agent, or Firm*—Wenderoth, Lind & Ponack

[57] ABSTRACT

The present invention provides an inspecting method and an apparatus therefor. A light illuminates an object to be inspected having optical diffusive characteristics such as a ceramics plate. A part of the light diffuses in the object from an illumination area is reflected at or passes through a defect such as a crack and reaches an imaging area. An image sensor detects the image of the imaging area. A signal showing a larger change is processed thereby to inspect the defect. The object is displaced stepwise relative to the light source and the image sensor. Thus, a crack or the like in an object can be inspected with high accuracy and at a high speed.

15 Claims, 8 Drawing Sheets

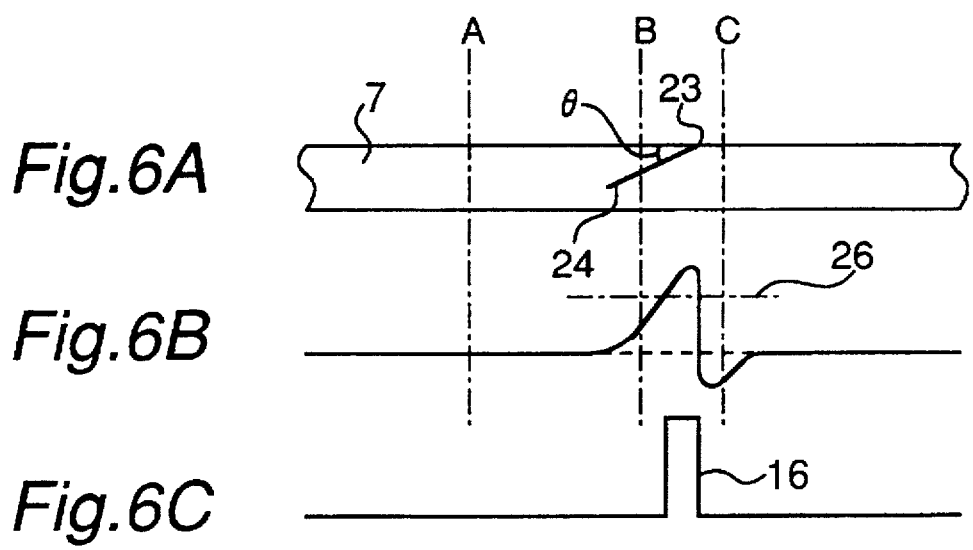
Fig.6A
Fig.6B
Fig.6C
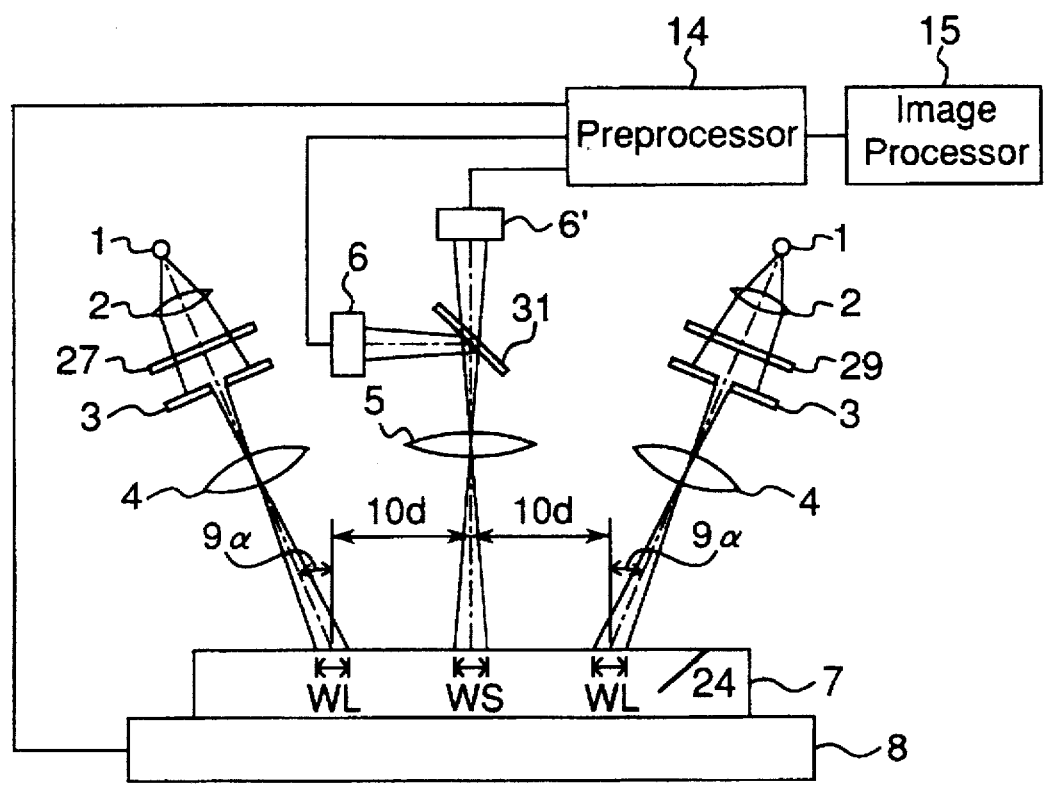
Fig.7

|  | Angle θ of Crack Plane | | |
|---|---|---|---|
|  | 0° → | 90° → | 180° |
| Small Crack Length L ↓ Large | Change in reflected light 14 < Change in reflected light 15 | Change in reflected light 14 > Change in reflected light 15 | |
|  | Change in reflected light 14 > Change in reflected light 15 | Change in reflected light 14 < Change in reflected light 15 | |

(Rotation 0°)

(Rotation 90°)

(Rotation 180°)

(Rotation 270°)

METHOD AND APPARATUS FOR OPTICAL INSPECTION

BACKGROUND OF THE INVENTION

1. Field of the Invention

The present invention relates to a method and an apparatus for optically inspecting optical non-uniformity inside an object to be inspected.

2. Description of the Prior Art

An example of conventional technology for inspecting defects in ceramics material will be described below. Various kinds of ceramics products, for example, insulating ceramics, piezoelectric ceramics and the like, are widely used in many mechanical parts including electronic parts. However, the brittle fracture of ceramics is now drawing attention. That is, minute defects present at the surface of a ceramics part or therein, or micro cracks having an opening width on the order of a submicron, become starting points to destroy it. Among these defects, cracks on the surface of a ceramic part are particularly brought into question. A limit of the length of a crack in practical use is generally considered to be 30–100 μm.

Although visual inspection by an optical microscope or the like has been used heretofore at production lines, the inspecting accuracy of the method is questionable because of the fact that the cracks to be detected are small in size and low in contrast. For example, Japanese Patent laid open Publication 4-16751/1992 describes a ceramics test method using an optical microscope. A light beam entering into a center of a field of view of a microscope in a ceramics sample or outside the field of view propagates inside the sample. If the light encounters a crack, within the field, the propagation of light is shielded by the crack, or the light does not cross the crack. Then, a boundary of a brighter region and a darker region observed in the field indicated the existence of a crack. However, the inhomogeneity of brightness near the crack depends on the relative position of the incident point of light to the crack, especially if a plurality of cracks exist in the field and interact with each other. Therefore, it is difficult to detect the crack or cracks precisely, or the inspection accuracy is low. U.S. Pat. No. 5,344,213 describes an inspection system, wherein a light beam enters into the edge of a sample in order to project substantially all light into the sample and a surface of the sample is observed with a charge coupled device or the like. Because the light enters at the edge, a sample to which the system applies is limited to a transparent plate or the like. Further, inspection accuracy of a defect becomes lower as the position of the defect is farther from the edge.

Meanwhile, for inspecting the defects, such methods as visual inspection using a microscope or the like, penetration flaw detection, ultrasonic flaw detection, ultrasonic microscopic detection, radiation flaw detection, etc. are carried out. The aforementioned penetration flaw detection, ultrasonic flaw detection, ultrasonic microscopic detection, radiation flaw detection, etc. have higher accuracy. However, an inspecting apparatus therefor is required to be highly accurate, high-speed and low-cost for the in-line inspection and a using substrate itself is limited to be inexpensive. Therefore, any of the above methods is not perfectly fit for the purpose.

SUMMARY OF THE INVENTION

An object of the present invention is to provide a method and an apparatus enabling inspection of defects, for instance, cracks or the like of an optically diffusive object to be inspected, such as a ceramic substrate or the like, with high accuracy at low costs and at high speeds.

In one aspect of the invention, light is cast through a slit to a first area in a surface of an object to be inspected such as a ceramics plate. The slit is preferably rectangular. Then, light radiating from a second area in the surface after penetrating the interior of the object is imaged with an image sensor such as a linear sensor. The second area is located so as not to overlap over the first area, or so that a light after penetrating through the object is imaged, except for the illumination light. The object is displaced stepwise relatively to the casting light and the linear sensor. The object is displaced stepwise relative to the first and second regions. Further, the object may be rotated, and an image may be taken at each rotation in this case. Image processing for detecting a defect is performed on the image data. For example, a change in intensity of the light is detected to inspect optical non-uniformity of the object. A ceramic substrate or the like has internal cracks or air bubbles enclosed therein, and the reflectance or transmittance is locally changed by the existence of the internal cracks or the air bubbles, and this causes optical non-uniformity. Such optical non-uniformity are enhanced by diffusion at defects and detected with high sensitivity, and even a defect having a size smaller than the pixel resolution can be detected.

In a second aspect of the invention, a plurality of lights having different wavelengths are cast through slits to a plurality of illumination areas in a surface of an object to be inspected. Then, light entering through the illumination areas into the object and radiating from an imaging area in the surface is imaged with a linear sensor. The optical paths of the two lights are different, and defects can be detected with higher accuracy. In a modified aspect of the invention, light is cast through a slit to a first area in a surface of an object to be inspected. Then, lights radiating from second and third areas in the surface after penetrating the interior of the object are imaged with linear sensors. The optical paths of the two lights are also different in this case, and defects can be detected with higher accuracy.

An advantage of the invention is that a defect in an object can be detected with high precision.

Another advantage of the invention is that a defect having a size smaller than pixel resolution can be detected.

BRIEF DESCRIPTION OF THE DRAWINGS

The above and other objects and features of the present invention will become clear from the following description taken in conjunction with the preferred embodiments thereof with reference to the accompanying drawings, throughout which like parts are designated by like reference numerals, and in which:

FIG. 6A is a sectional view of a sample, FIG. 6B is a diagram of detection signal, and FIG. 6C is a diagram of a signal binarized with a threshold level;

FIG. 7 is a diagram of an inspection apparatus according to a second embodiment of the present invention;

DETAILED DESCRIPTION OF THE PREFERRED EMBODIMENTS

Figure 1:
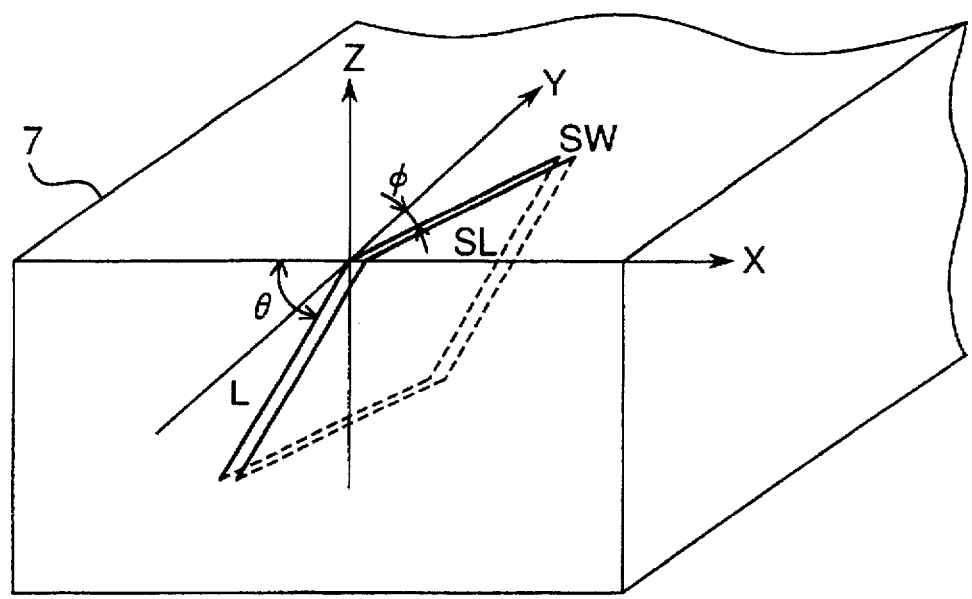
FIG. 1 is a perspective view, partly in section, of an object to be inspected.

Referring now to the drawings, wherein like reference characters designate like or corresponding parts throughout the several views, embodiments of the invention will be described in detail. A principle of optical inspection is explained first. A light penetrating through an object and radiating from a surface of the object includes optical information inside the object. For instance, if optical non-uniformity is present inside the object, it makes the reflectance or transmittance, etc. locally irregular, and the intensity of light radiating from the non-uniformity part of the surface differs from that of light radiating from other parts of the surface. The optical non-uniformity of the object is thus detected by detecting this intensity change.

The principle is explained with further reference to FIG. 1. In the following description with reference to FIG. 1, a direction of a plane of the crack is represented by an inclining angle $\theta$ and a direction angle $\phi$ of an opening of the crack. On the other hand, the size of the crack is indicated by a length L of the crack, a length SL of the opening of the crack and a width SW of the opening of the crack. It is to be noted here that a defect on the order of submicron for the width SW and tens of microns for the length L or a larger defect should be detected in the case of a ceramic object.

When the object diffuses light, a part of the light cast to an illumination area of the object is refracted to enter the object, and diffuses inside the object with the intensity thereof being attenuated exponentially. A part of the diffusion light inside the object reaches an imaging area and radiates from the surface of the object. The radiating light will be referred to as a diffusion radiation light herein.

The intensity of the diffusion radiation light is changed because of influences of not only the length SL and the width SW of the opening of the crack as data of the surface of the object, but the size of the crack and the direction of the crack plane including the length L of the crack, the inclining angle $\theta$ of the crack plane, and the direction angle $\phi$ of the opening as data of the interior of the object. Also, a change in the intensity of signals depending on the size of the crack in the object and the direction of the crack plane is detected by detecting the diffusion radiation light as above.

Accordingly, the intensity change of signals due to the crack defect is emphasized and moreover, an area in the vicinity of the crack opening becomes an area where the signal changes, so that the width SW of the opening, etc. appears to be spatially enlarged to facilitate the detection. Even an imaging system of a low magnification is allowed to detect fine cracks having the opening of the width SW smaller than the resolution thereof. The crack can be detected with high accuracy at high speeds. According to the inspecting method of the invention, even if the opening width of the crack is 0.3 µm, which is smaller than the limit of the resolution of the imaging system, the crack is spatially enlarged and therefore can be detected by the imaging system optically.

On the contrary, in a conventional method of detecting data of the crack, wherein an imaging area and the whole of the periphery of the object are illuminated with the use of an optical microscope, etc., the diffusion radiation light from each illuminated area is integrated, resulting in a weakened change of signals at the crack. The defect cannot be emphasized, unlike the present invention.

Figure 2:
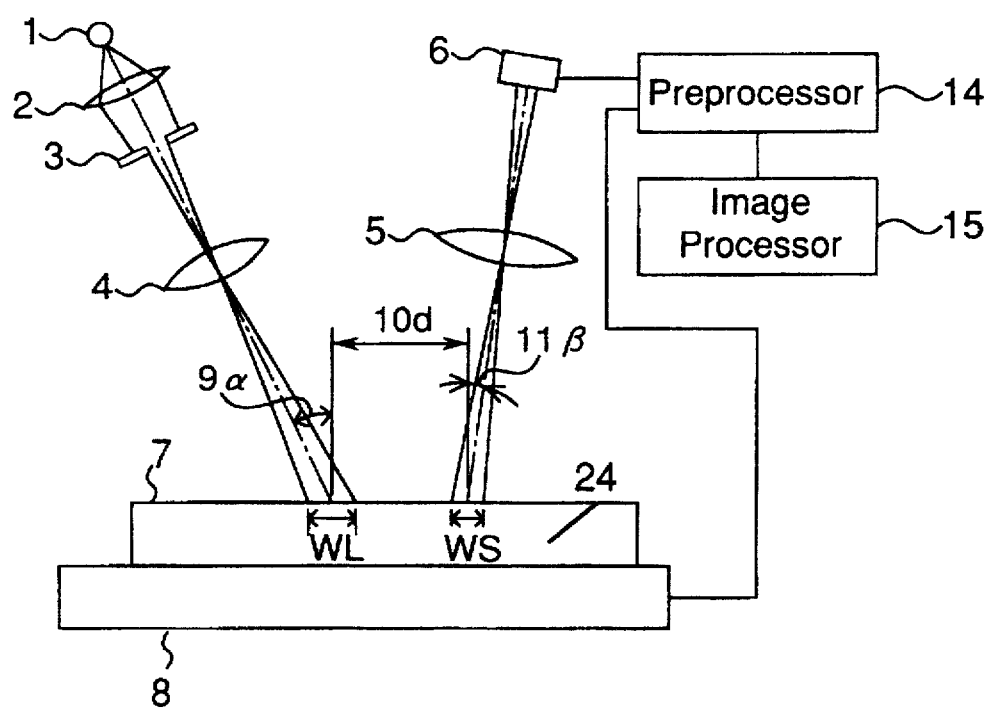
FIG. 2 is a diagram of an apparatus embodying an optical inspecting method according to a first example of the present invention.

Preferred embodiments of the present invention will be discussed hereinbelow. FIG. 2 shows a fundamental structure of an inspecting apparatus of an embodiment of the present invention. An illumination system of the apparatus is comprised of a white light source 1, a condenser lens 2, a shielding plate 3 having a rectangular slit, and a projection lens 4. An imaging system consists of an objective lens 5 and a linear sensor 6. A stage 8 is a sample stage on which an object to be inspected is placed and displaced stepwise. A preprocessor 14 forms an image from signals received from the linear sensor 6 and the moving system 8, while an image processor 15 processes the image.

On a surface of the object 7, an illumination area 12 has a width Wl, while an imaging area 13 has a width Ws. Angles $\alpha$ and $\beta$ denote angles of an optical axis of the illumination system and of an optical axis of the imaging system, relative to a normal of the surface of the object 7. The optical axes of the illumination system and the imaging system are spaced by a distance "d".

Supposing that a section in the imaging area 13 detected by each pixel of the linear sensor 6 in the imaging system via the optical system is denoted as a pixel resolution, the pixel resolution is obtained by dividing a size of the pixel by a magnification power. According to the first embodiment, the imaging area 13 of the width Ws is imaged by one pixel of the linear sensor 6 and therefore the width Ws corresponds to the pixel resolution. In the above-mentioned apparatus, when light from the white light source 1 passing through the condenser lens 2 illuminates the shielding plate 3, an image of the slit of the shielding plate 3 forms the illumination area 12 of the width Wl on the object 7. The illumination area 12 is accordingly similar in shape to the slit.

In detecting a radiation light from the surface of the object 7, which includes information about the inside of the object 7, it is a feature of the embodiment that the imaging area 13, to detect the radiation light, is set so as not to overlap with the illumination area 12. This arrangement prevents reflecting light from the illumination area 12 from mingling at the linear sensor 6, thus making it possible to detect only radiation light. More specifically, a minimum distance (d−Ws/2−Wl/2) between the illumination area 12 and imaging area 13 is set to have a positive value so as not to illuminate the imaging area 13.

A light diffused inside the object 7 and radiating from the imaging area 13 focuses an image on the linear sensor 6 by the objective lens 5 of the imaging system. While the object 7 is sequentially displaced by the moving stage 8, the image processor 15 processes an image signal formed by the preprocessor 14 from signals of the linear sensor 6 and signals from the moving stage 8. Thus, crack defects 24 in the object 7 can be detected.

Figure 3:
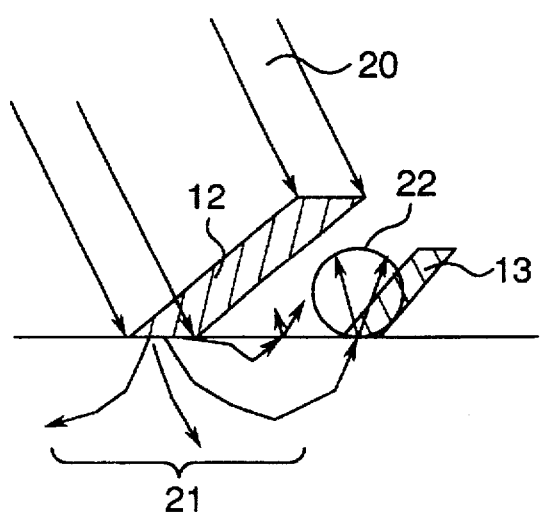
FIG. 3 is a perspective view, partly in section, of an object to be inspected for illustrating the diffusion of light into an illumination area and an imaging area on an object to be inspected.

FIG. 3 shows schematically an example of the diffusion of light from the illumination area 12 (illustrated with hatching) of a width ll to the imaging area 13 (illustrated with hatching) of the width Ws on the object 7. The illumination area 12 in the vicinity of the imaging area 13 is illuminated by a rectangular illumination light 20 by the above inspecting apparatus, whereas the imaging area 13 is not illuminated by the illumination light. In FIG. 3, the areas 12 and 13 extend on the surface of the object, while a section crossing through an end of the rectangular area 12 displays diffused light.

When the object 7 diffuses a light 20 cast on the illumination area 12, a part thereof is refracted to enter the interior of the object 7. The light is diffused inside the object 7, with its intensity attenuated exponentially. A part of a diffusion light 21 in the object 7 reaches the imaging—area 13 and radiates from the surface of the object 7. This radiation light 22 will be called diffusion radiation light.

Figure 4:
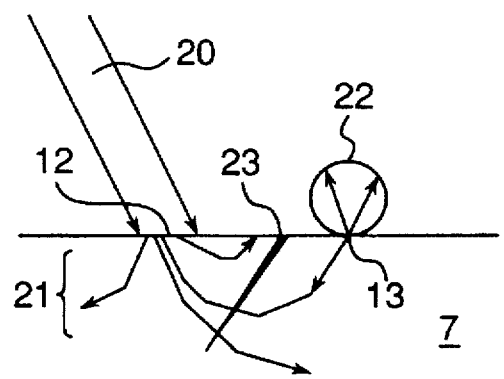
FIG. 4 is a diagram of the diffusion of light when a crack defect is present between the illumination area and imaging area.

As shown in FIG. 4, If a crack 24 has an opening 23 between the illumination area 12 and the imaging area 13, a part of the diffusion light 21 reaching the imaging area 13 after being diffused in the object 7 passes through the crack 24 before reaching the imaging area 13. Since the diffusion light passing the crack 24 is furthermore attenuated, the intensity of the diffusion radiation light 22 radiating from the imaging area 13 is decreased in comparison with the case where the crack 24 is not present.

Figure 5:
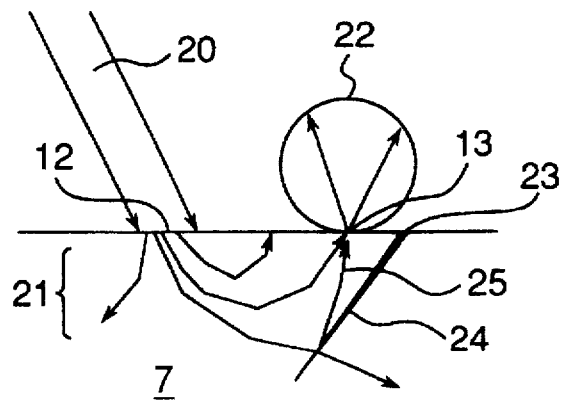
FIG. 5 is a diagram of the diffusion of light when a crack defect is present outside between the illumination area and imaging area.

Meanwhile, if a crack 24 is formed at a position shown in FIG. 5, and the opening 23 of the crack 24 is not located between the illumination area 12 and the imaging area 13, a part of the diffusion light 21 radiates as the diffusion radiation light from the surface of the imaging area 13 in the same fashion as when the crack 24 is not present. In addition, a part 25 of the diffusion light 21 from the illumination area 12 is reflected at the crack 24 to reach the imaging area 13. As a result, when the crack 24 is located at the position indicated in FIG. 5, the intensity of the diffusion radiation light 22 radiating from the imaging area 13 is eventually increased as compared with that of the examples shown in FIGS. 3 and 4.

Next, an example of how to detect cracks in an object will be discussed below on the basis of the foregoing description when the crack 24 is present at the right side of the object 7 as shown in FIG. 2. FIGS. 6A–6C show diagrams for explaining an imaging result. The object 7 on the sample stage is sequentially displaced left by the moving stage 8 in a direction shown by an arrow.

FIG. 6A shows a section of the object 7 sequentially imaged from left to right according to the above inspecting method, and it has a crack 24 with an angle θ of the crack plane relative to the surface. FIG. 6B indicates an imaging signal obtained by each pixel of the linear sensor 6 before and after the crack 24 at a part of the object 7 that passes the imaging area 23 during the displacement of the object 7 from left to right. Considering imaging areas A, B and C in the object 7 shown in FIG. 6A, the imaging area A includes no crack and therefore the signal is not influenced by the crack 24, and the light is diffused in the manner exactly as shown in FIG. 3. A signal of the linear sensor 6 stays at a reference level without being influenced by the crack 24. At the imaging area B, the diffusion radiation light includes also the light 25 reflected at an interface of the crack as described before with reference to FIG. 5. Therefore, the level of the signal of the linear sensor 6 is increased in correspondence to the intensity increase in the diffusion radiation light. At the imaging area C, the imaged diffusion radiation light has its intensity reduced because the crack shuts the light as described with reference to FIG. 4, whereby the level of the signal from the linear sensor 6 is decreased. If the crack is present in the vicinity of the imaging area B or C, the signal is subject to change, as is clear from FIG. 6B, even though the opening 23 is outside the imaging area. Such signals are affected not only by the openings of the cracks at the surface, but also by sizes of the cracks and directions of the crack planes inside the object.

The signal change shown in FIG. 6B takes place surely even when the crack has a mere width on the order of a submicron. Moreover, the detection of the signal change does not particularly require a high sensitivity, nor a high S/N in ordinary use. The signal change can be imaged, for example, by a conventional CCD imaging apparatus. That is, the signal change of FIG. 6B can be confirmed on a monitor screen in the conventional CCD imaging device as a clear contrast ratio. Accordingly, in the inspecting method of the present embodiment, the presence/absence of a crack of a submicron width and a position of the crack can be recognized or detected in the form of a clear contrast ratio on the monitor screen of the imaging device.

Needless to say, the image processor 15 may set a suitable threshold value 26 on the signal of FIG. 6B, so that the signal is binarized to detect a high-lighted crack 16, as shown in FIG. 6C. In this case, the high-lighted crack 16 can be detected and displayed as a defect having a larger size than the opening 23 at the surface data of the crack 24. Since the above signal characteristics emphasize the intensity change in signals due to the crack 24 and the signal change is observed also in the vicinity of the crack 24, the crack 24 is magnified and emphasized thereby to facilitate the detection.

For example, even when the opening 23 of the crack 24 has a width SW on the order of submicron, the signal characteristics as above are obtainable according to the present inspecting method, so that the crack can be detected at several µm to several tens µm of pixel resolution. Therefore, even an imaging system of a low magnification that has a larger pixel resolution than the size of a crack to be detected can detect a minute crack smaller than the pixel resolution.

When a two-dimensional CCD imaging element is used for detecting the light (batch processing), a two-dimensional imaging area is in inverse proportion to a square of the magnification power, and the two-dimensional area to be inspected may be enlarged for an imaging system having a lower magnification, to thereby improve an inspection speed. The inspection is hence conducted with high accuracy at a high speed.

If differentiation is carried out before the abovementioned binarization, a position where a primary differential value becomes maximum is where the opening 23 is located in the imaging area, and therefore the position of the opening 23 can be specified accurately.

Although the linear sensor 6 having CCD elements aligned linearly is used as an imaging means in the first embodiment, other means than the CCD elements may be employable.

Next, a second embodiment of the invention is explained. FIG. 7 indicates a fundamental structure of an inspecting apparatus of the second embodiment of the invention. An illumination system consisting of a white light source 1, a condenser lens 2, a first band pass filter 27 of a first wavelength band "a", a rectangular slit 3 and a projecting lens 4 is disposed at the left side of an imaging optical axis. Another similar illumination system is arranged at a position symmetric to the above illumination system with respect to the imaging optical axis, and it is different from the first one by a second band pass filter 29 of a second wavelength band "b" used instead of the first filter 27.

A color-separating imaging system located between the two illumination systems is composed of an objective lens 5, a dichroic mirror 31 for separating lights of the two wavelength bands "a" and "b", and two linear sensors 6, 6' corresponding to signals of the two wavelength bands.

A moving stage 8 displaces a sample stage stepwise on which an object 7 to be inspected is placed. A preprocessor 14 forms images of the two wavelength bands "a" and "b" from signals of the linear sensors 6, 6' and signals from the moving stage 8. An image processor 15 processes images supplied from a preprocessor 14.

On a surface of the object 7, an illumination area 28 has a width W1 illuminated by the light of the first wavelength band, another illumination area 30 has a width W1 illuminated by the light of the second wavelength band, while an imaging area 13 has a width Ws. Angle α denotes an angle of an optical axis of the illumination systems relative to a normal of the surface of the object 7. The optical axes of the illumination systems are spaced by a distance "d" from the optical axis of the imaging system. The width Ws of the imaging area 13 corresponds to pixel resolution.

In the above-described apparatus, a light from the white light source 1 passes through the condenser lens 2, and either the wavelength band "a" or "b" is selectively passed through the band pass filter 27 or 29 to illuminate the slit 3. An image of the slit 3 is formed by the projecting lens 4 into the illumination area 28, 30 of the width W1 on the object 7 which area is similar in shape to the slit 3. A minimum distance (d−Ws/2−W1/2) between each illumination area 28, 30 and the imaging area 13 is set to have a positive value so that the illumination light does not enter into the imaging area 13.

A diffusion radiation light of the light of the first wavelength band "a" diffused in the object 7 from the illumination area 28 and radiating from the imaging area 13, and another diffusion radiation light of the second wavelength band "b" diffused in the object 7 from the illumination area 30 and radiating from the imaging area 13, pass the objective lens 5 and are separated in color by the dichroic mirror 31 in the imaging system, forming images on the corresponding linear sensors 6, 6'.

While the object 7 is sequentially displaced stepwise by the moving stage 8, the preprocessor 14 forms images of the wavelength bands "a" and "b" from signals of the linear sensors 6, 6 and of the moving stage 8, and the image processor 15 processes the image signals received from the preprocessor 14 to inspect a crack defect.

Figures 8, 9:
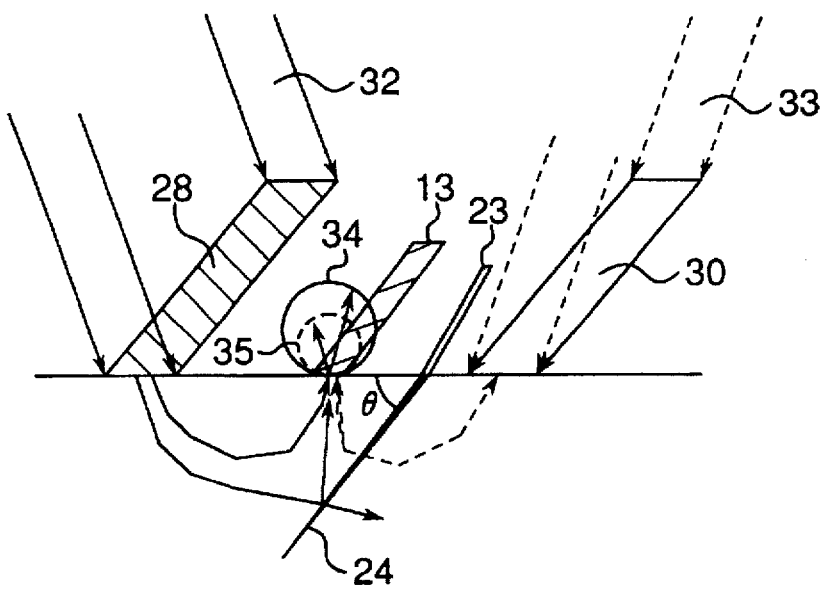
FIG. 8 is a perspective view, partly in section, of an object with the diffusion of light from two illumination areas having wavelength bands not overlapping each other.
FIG. 9 is a diagram showing a relationship between diffusion radiation lights from two illumination areas and the shape of a crack.

FIG. 8 shows an example of the diffusion of light to the imaging area 13 (illustrated with hatching) on the surface of the object 7. With the use of the inspecting apparatus shown in FIG. 7, an illumination light 32 of the wavelength band "a" is cast to the generally rectangular illumination area 28 on the object 7 (illustrated with hatching), while another illumination light 33 of the wavelength band "b", not overlapping with the wavelength band "a", is cast to the generally rectangular illumination area 30 not overlapping with the area 28. When the object 7 diffuses light, parts of the illumination light hitting the areas 28 and 30 are refracted and diffused in the object 7, while being attenuated. Subsequently, a part of the internal diffusion light radiates from the surface of the imaging area 13 as a diffusion radiation light 34 of the wavelength band "a" and a diffusion radiation light 35 of the wavelength band "b".

If a crack defect 24 is present in the object 7, a part of the diffusion light of the wavelength band "a" from the illumination area 28 is reflected by or passes through the crack 24 to eventually reach the imaging area 13. On the other hand, a part of the diffusion light of the wavelength band "b" from the illumination area 30 is likewise reflected at or passes through the crack 24 to reach the imaging area 13. Because of the different routes for the illumination lights of the wavelength bands "a" and "b" to reach the imaging area 13, intensities of the diffusion lights are changed differently by the reflection and refraction due to the crack 24. In consequence, the intensity change of each diffusion radiation light 34, 35 caused by the crack 24 shows such qualitative characteristics as summarized in FIG. 9, depending on the inclining angle θ of the crack plane and the length L of the crack 24.

Figure 10A:
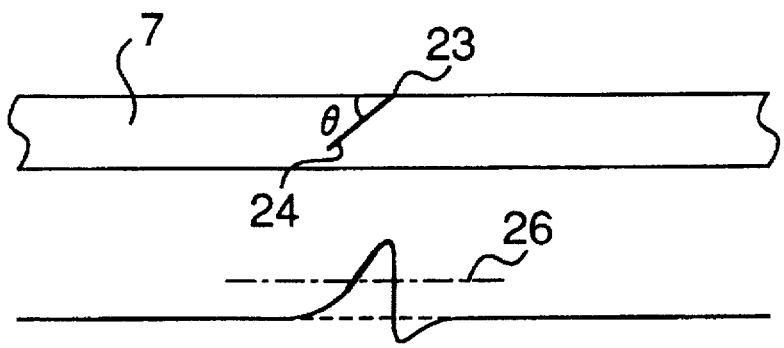
FIG. 10A is a sectional view of an object to be inspected.

A method of detecting crack defects according to the second embodiment of the present invention will be detailed based on the above description. The crack 24 is at the right side of the object 7 in FIG. 7. FIGS. 10B–10F show diagrams of image data when the object 7 on the moving stage 8 is imaged while being sequentially displaced left. The object 7 to be inspected is shown in FIG. 10A, and it is sequentially imaged from left to right by the linear sensors 6, 6'.

Figure 10B:
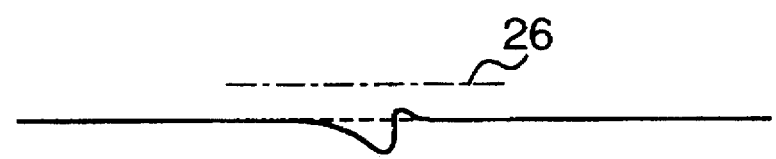
FIGS. 10B and 10C are diagrams of crack detection signals.
Figure 10C:
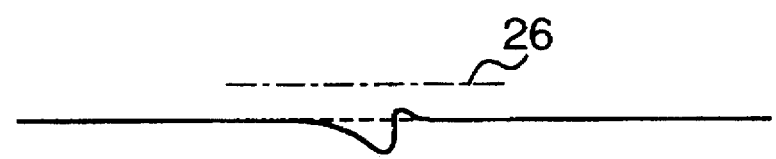
Figure 10D:
FIGS. 10D and 10E are diagrams of signals binarized with a threshold level.
Figure 10E:

FIG. 10B shows an image signal of the wavelength band "a" obtained by each pixel on the linear sensor when the crack 24 at a part of the object 7 is imaged during the sequential displacement of the object from left to right, while FIG. 10C shows that of the wavelength band "b". Any of the signals has a characteristic changing in accordance with a relative position of the opening 23 of the crack 24. However, the illumination areas are different for each wavelength "a", "b". The direction of the crack plane and the size of the crack, which will influence the diffusion of light to the imaging area, are different at each illumination area, as already discussed with reference to FIGS. 8 and 9. Therefore, the signal change shows different characteristics in different amounts for each wavelength.

Figure 10F:
FIG. 10F is a diagram of a sum of the signals shown in FIGS. 10D and 10E.

Each signal is binarized by a suitable threshold value 26 at the image processor 15, to thereby detect the defect. The detection results with the wavelength bands "a" and "b" are respectively indicated in FIGS. 10D and 10E. From these data shown in FIGS. 10D and 10E, the crack 24 can be detected by the signal of the wavelength band "a", whereas it is found impossible by the signal of the wavelength band "b". In other words, a detecting accuracy is not uniform among the signals. For solving the above inconvenience, a logical sum of the detection results at the respective wavelength bands is operated, as shown in FIG. 10F, for a final judgment. Accordingly, the crack 24 in various kinds of shapes can be inspected accurately in the second embodiment.

According to the second embodiment of the present invention, after the diffusion radiation lights 34, 35 of the wavelength bands "a" and "b" are imaged, the image signal showing a larger intensity change among the image signals of every wavelength band is processed. Therefore, the intensity change of signals due to the crack 24 of any shape is highlighted and, at the same time, the signal change is detected also in the vicinity of the crack. The crack 24 can thus be emphasized and detected easily. Therefore, even an imaging system of a low magnification having a pixel resolution relatively larger than the size of a crack to be detected can detect a minute crack smaller than the pixel resolution.

Since a two-dimensional imaging area in batch processing using a two-dimensional CCD imaging element is inversely proportional to a square of the magnification power, if the two-dimensional area to be inspected at one time are enlarged in an imaging system with a lower magnification to improve an inspecting speed, the defect can be inspected highly accurately at a high speed.

Moreover, if a differential signal of the image signals is obtained before the binarization process, the signal change due to the crack defect can be emphasized to thereby improve an inspecting accuracy. If differentiation is executed before the binarization, a position of the maximum primary differential value corresponds to a position where the opening 23 of the crack is located in the imaging area. Then, it is possible to specify the position of the opening 23 accurately.

In place of the color-separating optical system shown in FIG. 7, two band pass filters 27 and 29 of the two wavelength bands, and a single linear sensor 6 may be employed. In this case, the band pass filters 27, 29 may be switched in turn to image the object.

Alternatively, in place of the color-separating optical system of FIG. 7, an optical system of a single linear sensor may be used wherein at least two band pass filters of two wavelength bands are regularly disposed to each pixel of the linear sensor 6.

The linear sensors 6, 6' having CCD elements aligned in a line are used as an imaging means in the second embodiment, but the imaging elements may be other than the CCD elements.

Figure 11:
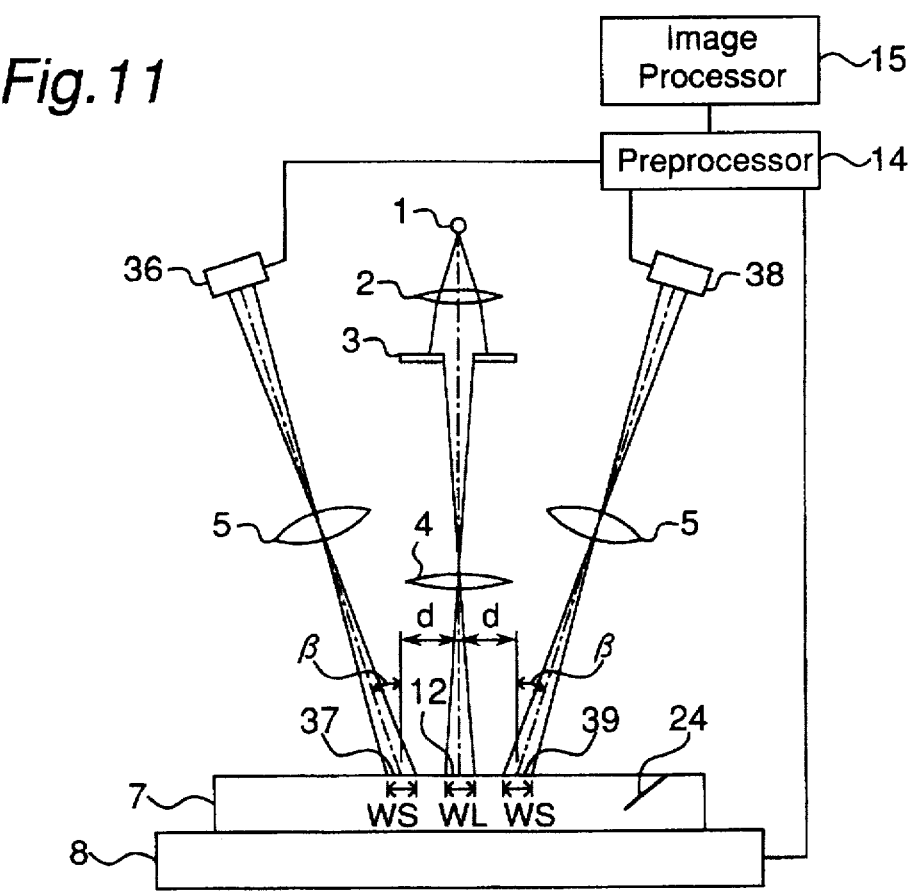
FIG. 11 is a diagram of an inspection apparatus according to a third embodiment of the present invention.

Next, an inspection method of a third embodiment of the invention is explained. FIG. 11 shows a fundamental structure of the inspecting apparatus. An illumination system comprises a white light source 1, a condenser lens 2, a rectangular slit 3 and a projecting lens 4, and an optical axis of the light incident onto an object 7 is in parallel to a normal of the surface of the object 7. A first imaging system comprising an objective lens 5 and a linear sensor 36 is placed at the left side of an optical axis of the illumination system, and a second imaging system comprising an objective lens 5 and a linear sensor 38 is arranged symmetrically to the first imaging system with respect to the optical axis. The object 7 is placed on a moving stage 8. A preprocessor 14 forms images from signals of the two linear sensors 36, 38 and a signal from the moving system 8, and an image processor 15 processes the images from the preprocessor 14.

On the surface of the object 7, an imaging area 37 has a width Ws formed by the first imaging system, while an imaging area 39 has a width Ws formed by the second imaging system. An angle β denotes an angle of an optical axis of each imaging system to the normal of the surface of the object 7. A distance "d" denotes a spacing between optical axes of the illumination system and the imaging system. An illumination area 12 has a width Wl. The width Ws of each imaging—area corresponds to pixel resolution.

In the inspecting apparatus, a light from the white light source 1 passes the slit 3 and the condenser lens 2. An image of the slit 3 generates the illumination area 12 on the object 7 by the projecting lens 4. The illumination area 12 has the width Wl in a shape similar to that of the slit. A minimum distance (d−Ws/2−Wl/2) between the illumination area 12 and the imaging area 37, 39 is set to have a positive value in order not to send the illumination light to the imaging areas 37 and 39.

A diffusion radiation light diffused from the illumination area 12 into the object and radiating from the imaging area 37 focuses an image on the linear sensor 36 by the objective lens 5 of the first imaging system. Similarly, a diffusion radiation light diffused in the object from the illumination area 12 and radiating from the imaging area 39 focuses an image by the objective lens 5 of the second imaging system on the linear sensor 38.

While the object 7 is sequentially displaced by the moving stage 8, the preprocessor 14 forms images from signals of the linear sensors 36 and 38 and the moving system 8, and the image processor 15 processes the image signals received from the preprocessor 14 to detect a defect.

Figure 12:
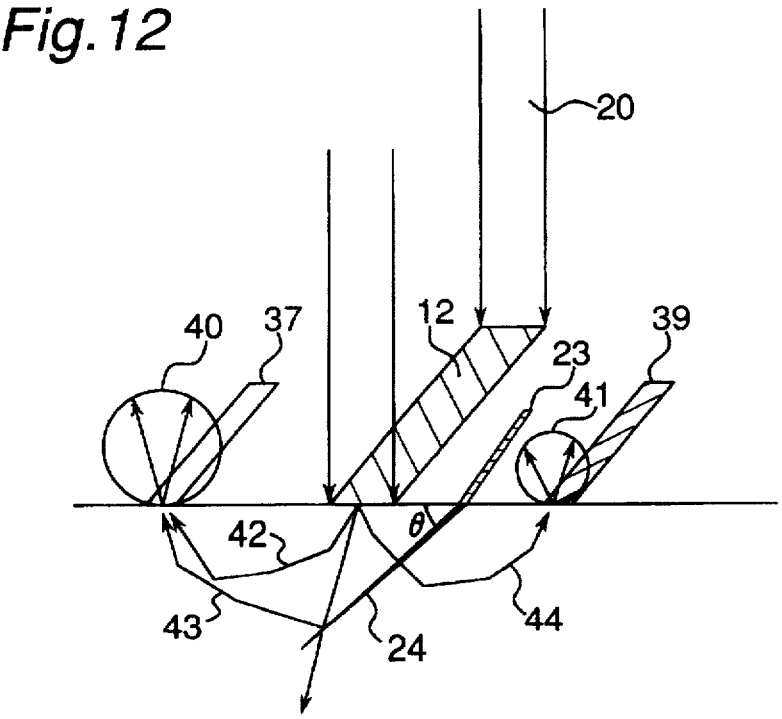
FIG. 12 is a perspective view, partly in section, of an object with the diffusion of light to two imaging areas from an illumination area.

FIG. 12 shows an example of optical paths of the diffusion of light to the imaging areas 37 and 39, respectively at the left and right sides of the illumination area 12, when the rectangular illumination area 12 on the object 7 is illuminated by a light 20 in the above inspecting apparatus. When the object 7 diffuses light, a part of the illumination light 20 cast to the illumination area 12 is refracted into the object and diffused in the object 7 while being attenuated. A part of this internal diffusion light radiates as a diffusion radiation light 40 from the imaging area 37 and as a diffusion radiation light 41 from the imaging area 39.

If the opening 23 of a crack 24 is present at a position indicated in FIG. 12, a part 42 of the internal diffusion light from the illumination area 12 is sent to the imaging area 37 without being influenced by the crack 24. Moreover, a part 43 of the internal diffusion light is reflected by the crack 24 and reaches the imaging area 37. As a result, the intensity of the diffusion radiation light 40 radiating from the imaging area 37 is enhanced. In contrast, a part 44 of the internal diffusion light reaches the imaging area 39 after passing through the crack 24. The intensity of the diffusion light is accordingly attenuated. The diffusion radiation light 41 radiating from the imaging area 39 includes the intensity decrease as above. Since the diffusion routes for the internal diffusion light reaching the imaging areas 37 and 39 are different, the intensity of each diffusion light is influenced and changed differently through the reflection and refraction at the crack 24.

Consequently, the intensity change of each diffusion radiation light 40, 41 due to the crack 24 shows the same characteristics as in FIG. 9 referred to in the description of the second embodiment. The image signals obtained by each linear sensor varies with the relative position of the opening of the crack 24, similar to those in the second embodiment. The signal change differs depending on the inclining angle θ of the crack plane and the length L of the crack, resulting in a difference in inspecting accuracy between the image signals.

An appropriate threshold value is set for such image signals at the image processor 15. Each image signal is binarized to thereby emphasize the defect. By taking the logical sum of defect detection results of the image signals at a last stage, the intensity change of signals due to the crack 24 is emphasized for any shape, specifically, any inclining angle θ of the crack plane and any length L of the crack. Simultaneously, because the signal change also occurs in the vicinity of the crack, the crack 24 is magnified and emphasized at the detecting time. Accordingly, even an imaging system of a low magnification power, which has a relatively large pixel resolution to the size of a crack to be detected, is allowed to detect a crack smaller than the pixel resolution.

Since a two-dimensional imaging area in batch processing using a two-dimensional CCD imaging element is inversely proportional to a square of the magnification power, if the two-dimensional area to be inspected at one time are enlarged in an imaging system with a lower magnification to improve an inspecting speed, the defect can be inspected highly accurately at a high speed.

If a differential signal of the image signals is obtained prior to the binarization process, the signal change due to the crack is emphasized and an inspection accuracy is improved.

If differentiation is carried out before the binarization, a position where a primary differential value becomes maximum is where the opening 23 of the crack is present in the imaging area. A position of the opening 23 is accordingly specified with good accuracy.

The linear sensors 36 and 38 are CCD linear sensors. However, the imaging means may be other elements than the CCD elements.

Since the illumination light used in the second embodiment is in the wavelength bands "a" and "b", the intensity of the diffusion light inside the object may be extraordinarily attenuated depending on the color of the object. This imposes an undesirable limit on the wavelength bands to be used. On the contrary, the third embodiment achieves equally accurate or more highly accurate inspection of defects with the same illumination light while the color of the object is not bounded.

Figure 13:
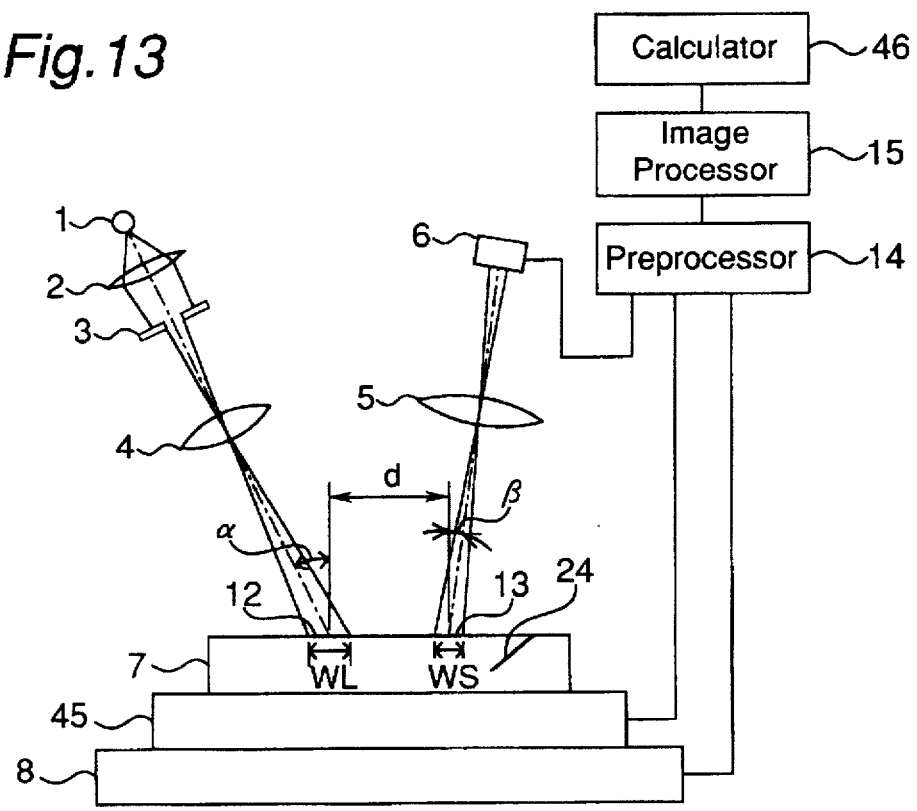
FIG. 13 is a diagram of an inspection apparatus according to a fourth example of the present invention.

Next, an inspecting apparatus of a fourth embodiment of the invention is explained. FIG. 13 shows a fundamental structure of the inspecting apparatus. An illumination system is comprised of a white light source 1, a condenser lens 2, a rectangular slit 3 and a projecting lens 4. On the other hand, an objective lens 5 and a linear sensor 6 constitutes an imaging system. A moving stage 8 displaces a sample stage stepwise in x and y directions, and a rotational system 45 put on the moving stage 8 rotates a sample stage 7. A preprocessor 14 forms images from signals of the linear sensor 6 and the moving system 7. An image processor 15 processes the image received from the preprocessor 14. A coordinate conversion calculator 46 calculates the coordinates of a position of a defect on the object in the image received from the image processor 15.

On the surface of the object 7, an illumination area 12 has a width w1 on an object to be inspected, and an imaging area 13 has a width Ws on the object. An angle α denotes of an angle of an optical axis of the illumination system relative to a normal of the surface of the object 7, and an angle β denotes an angle of an optical axis of the imaging system relative to the normal. A distance "d" on the object denotes a spacing between the optical axes of the illumination and imaging systems.

In the apparatus, when a light from the white light source 1 is cast to the slit 3 through the condenser lens 2, an image of the slit 3 forms the illumination area 12 of the width we on the object 7. The illumination area 12 is similar in shape to the slit. In order to prevent the entry of the illumination light to the imaging area 13, a minimum distance (d−Ws/2−W1/2) between the illumination area and the imaging area is set to have a positive value.

A diffusion radiation light entering from the illumination area 12, diffused inside the object 7 and radiating from the imaging area 13, focuses an image on the linear sensor 6 by the objective lens 5 of the imaging system. When the object 7 is sequentially displaced by the x-y moving system 8, image signals input to the image processor 15 via the preprocessor 14 are processed to detect a defect.

Then, the object 7 is rotated an optional angle δ by the rotation system 45. The illumination area is consequently displaced with respect to the imaging area 13. In this state, a crack defect is inspected by using the same procedure. The object 7 is sequentially rotated afterwards every optional angle δ and finally rotated (360-δ)° for inspection.

Figure 14A:
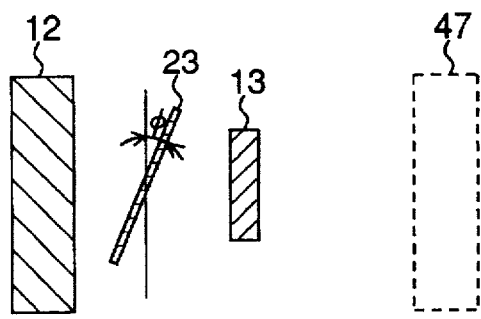
FIGS. 14A and 14B are a plan view and a sectional view of an illumination area, an imaging area and a position of a crack defect in an object to be inspected.
Figure 14B:
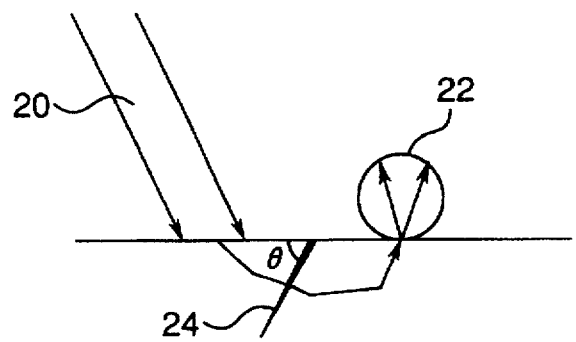

FIGS. 14A and 14B show an example of the diffusion of light to the imaging area 13 from the illumination area 12 when the rectangular illumination area 12 on the object 7 is illuminated by an illumination light 20 in the apparatus shown in FIG. 13. In case that the object 7 diffuses light, a part of the illumination light 20 cast to the illumination area 12 is refracted into the object 7 and diffused therein while being attenuated in intensity. Then, a part of the internal diffusion light radiates as a diffusion radiation light 22 from the imaging area 13. The illumination area 12 is then sequentially rotated and displaced with respect to the imaging area 13 to a position 47. The diffusion radiation light 22 radiating from the surface of the object 7 is imaged every time and a signal showing the maximum change is processed, to detect the defect.

FIG. 15 shows an example of how to detect a crack defect in the embodiment and will be discussed hereinbelow, assuming that a crack 24 is present at the right side of the object 7 as shown in FIG. 13. FIG. 15A illustrates the example when the object 7 is imaged during the sequential displacement of the sample stage to the left. The crack 24 having a length L in the object 7 shown in FIG. 15A has an opening 23 of a direction angle φ. A plane of the crack 24 is inclined an angle θ. In FIG. 15A, y-axis direction is a longitudinal direction of the linear sensor, and x-axis direction is a direction in which the sample stage 8 is displaced stepwise when the images are input. In imaging the object 7, the sample stage 8 is sequentially displaced in the x-axis direction from the left side of the object 7, and then, the object 7 is rotated every optional angle δ (every 90° in case of FIG. 15A) by the rotation system 45.

FIGS. 15B–15E show examples of image signals obtained by each pixel on the linear sensor 6 when the object 7 is sequentially imaged from left to right. Since the direction of the crack plane or size of the crack which influences the diffusion of light to the imaging area is different at each illumination area, signals are changed differently. Signals obtained at the linear sensor are greatly changed depending on a relative position of the opening 23, and the change in the signals varies with the direction angle φ of the opening, inclining angle θ of the crack plane, length L of the crack, etc., thereby causing the inspecting accuracy to be irregular.

A proper threshold value is set for each signal at the image processor 15 shown in FIG. 13, so that the signal is binarized to emphasize the defect. A logical sum of detection results at respective rotary angles is obtained for final judgment. As described hereinabove, the intensity change in signals due to the crack 24 is emphasized by any kind, i.e., any direction angle φ of the opening, any inclining angle θ of the crack plane and any length L. At the same time, the signal also changes in the vicinity of the crack. Accordingly, the magnified and emphasized crack 24 is detected with high accuracy.

Even an imaging system of a low magnification power which has a pixel resolution relatively larger than the size of a crack to be detected can detect a crack smaller than the pixel resolution.

Since the imaging area during the batch processing is inversely proportional to a square of the magnification power, the area to be inspected at one time may be enlarged in an imaging system of a lowered magnification, and this improves an inspecting speed. The defects are inspected with high accuracy at a high speed.

Although the object 7 is rotated by the rotational system 45, the illumination system and imaging system may be rotated altogether for this purpose.

A position of the defect on the object can be calculated by converting the position to x and y coordinates at a reference rotary angle of the object by the coordinate conversion calculator 46.

A primary differential obtained prior to the binarization becomes maximum at a position where the opening 23 of the crack is present in the imaging area. Therefore, a position of the opening 23 can be accurately specified.

The linear sensor 6 in the fourth embodiment has CCD elements aligned in a line. However, an imaging means may be constituted of other elements than the CCD elements.

The rotational system 45 and the coordinate conversion calculator 46 may also be added to the systems shown in FIGS. 6 and 10, as will be understood easily by a person skilled in the art, and such modifications are not explained here to avoid repetition of explanation.

In each of the inspecting apparatuses shown in FIGS. 2, 7, 11 and 13, the illumination light passing through the rectangular slit of the illumination system may be converged into a rectangular shape by a cylindrical lens so as to form a generally rectangular illumination area on the object. According to this arrangement, the change in the detection signals is furthermore emphasized because of the width W1 of the illumination area being reduced without decreasing the intensity of the incoming light, and therefore, the crack can be detected with an improved accuracy.

The present invention has been described in detail with reference to the preferred embodiments thereof. Although the present invention is applied to detection of cracks in a ceramic substrate in each embodiment, the present invention is not limited to the foregoing embodiments because the detection principle of the present invention is based on the light penetrating the object to be inspected and radiating from the surface of the object which includes data of an optical ununiformity inside the object. For instance, an interface or the like of a high reflectance or a low transmittance which is locally present inside the object can be detected according to the present invention.

Figure 15A:
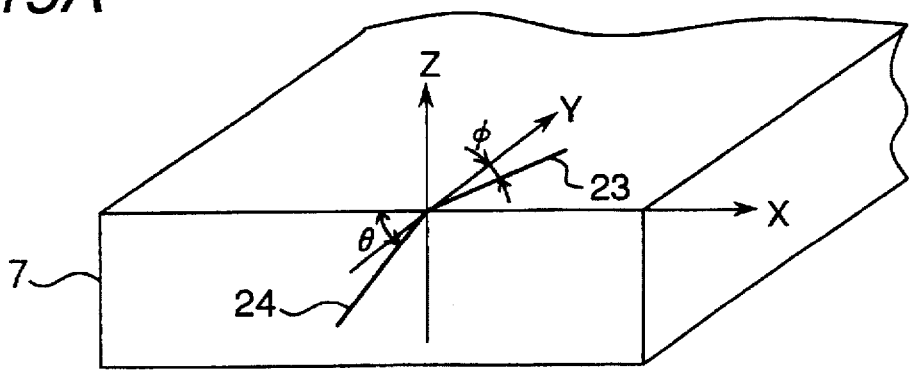
FIG. 15A is a perspective view, partly in section, of an object to be inspected.
Figure 15B:
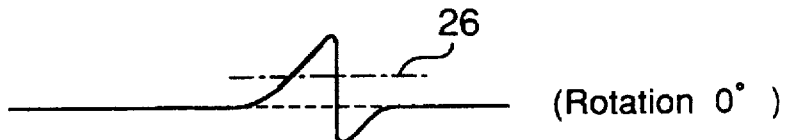
FIGS. 15B, 15C, 15D and 15E are diagrams of crack detection signals at four rotation angles of 0, 90, 180 and 270°.
Figure 15C:
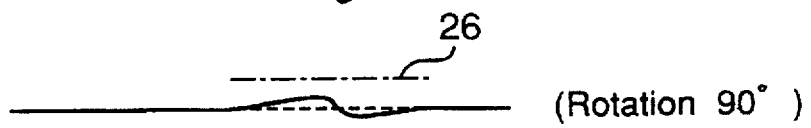
Figure 15D:
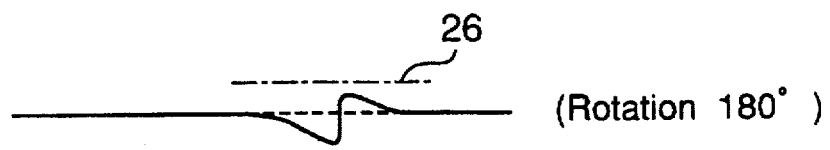
Figure 15E:
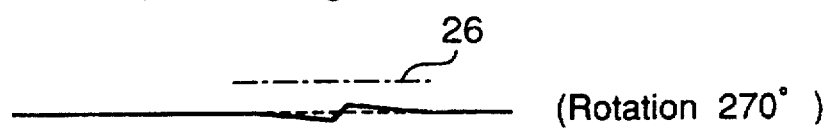

The imaging area and the whole peripheral area are illuminated in the conventional method using a microscope or the like. Therefore, the crack as shown FIG. 15A would be represented by a signal which is an integration of signals of FIGS. 15B–15E from different illumination areas. As a result, since the signals of approximately inverse polarities as shown in FIGS. 15B and 15D are offset, the signal change at the crack is decreased. The defect is hard to inspect with eyes according to the prior art, which problem cannot be solved even by a high magnification power.

In contrast, the inspecting method and inspecting apparatus of the present invention are based on the fact that the intensity of the diffusion radiation light diffused from the limited illumination area to the imaging area and radiating from the surface of the object is changed by the crack present in the imaging area and in the periphery of the area. Then, the crack is emphasized to facilitate the detection. Even if the imaging system has several μm to several tens μm pixel resolution, the opening of the crack can be detected on the order of a submicron. The present invention is hence effective to inspect cracks and the like defects of the object showing diffusive characteristics, with high accuracy at high speeds and at low costs.

Although the present invention has been fully described in connection with the preferred embodiments thereof with reference to the accompanying drawings, it is to be noted that various changes and modifications will be apparent to those skilled in the art. Such changes and modifications are to be understood as included within the scope of the present invention as defined by the appended claims unless they depart therefrom.

What is claimed is:

1. An optical inspecting method for detecting optical non-uniformity in an object, comprising the steps of:

(a) casting light to a first area on a surface of an object so as to penetrate the object with the light;

(b) detecting radiating light radiating from a second area on the surface of the object after the cast light has penetrated into the object from the first area;

(c) detecting a change in the intensity of the radiating light that has been detected;

(d) displacing the object stepwise relative to the cast light so as to move the first and second areas on the surface of the object each time said steps (a)–(c) are performed; and (e) sequentially rotating the first area relative to the second area and detecting the light radiating from the second area for each sequential rotation.

2. The method of claim 1, wherein said steps (a)–(d) are repeated for each sequential rotation.

3. The method claim 2, wherein said steps (a)–(d) are repeated a plurality of times for each sequential rotation.

4. An optical inspecting method for detecting optical non-uniformity in an object, comprising the steps of:

(a) casting a plurality of different kinds of lights having wavelength bands not overlapping each other onto a plurality of first areas on a surface of an object, the first areas also not overlapping each other;

(b) detecting the radiated light radiating from a second area on the surface of the object after the cast light has penetrated through the object; and (c) detecting a change in the intensity of the detected radiated light.

5. The method according to claim 4, and further comprising the step of displacing the object stepwise relative to the cast light so as to move the first and second areas on the surface of the object each time said steps (a)–(c) are performed.

6. The method according to claim 4, wherein the first and second areas do not overlap each other.

7. The method according to claim 4, wherein the first areas are rectangular, the second area is rectangular, and one of the first areas is located on one side of the second area, while the other of the first areas is located on the other side of the second area.

8. An optical inspecting method for detecting optical non-uniformity in an object, comprising the steps of:

(a) casting light on a first area on a surface of an object so as to penetrate the object with the light;

(b) detecting radiated light radiating from a plurality of second areas on the surface of the object after the cast light has penetrated the object; and (c) detecting a change in the intensity of the detected radiated light;

wherein the first area is rectangular, the number of the plurality of second areas is two, and the two second areas are provided on opposite sides of the first area.

9. An optical inspecting method for detecting optical non-uniformity in an object, comprising the steps of:

(a) casting light onto a first area on a surface of an object;

(b) detecting radiated light radiating from a plurality of second areas on the surface of the object after the cast light has penetrated through the object;

(c) detecting a change in the intensity of the detected radiated light; and (d) stepwise displacing the object relative to the cast light so as to move the first area and the second areas on the surface of the object each time said steps (a)–(c) are performed.

10. The method according to claim 9, and further comprising the step of:

(e) sequentially rotating the first area relative to the second areas and detecting the light radiating from the second areas for each sequential rotation.

11. An optical inspecting apparatus comprising:

an illumination system for projecting a light through a slit onto a first area on a surface of an object to be inspected;

an imaging system comprising a linear sensor for detecting an image of a second area on the surface of the object, the second area not overlapping the first area;

a driving system for displacing the object relative to said imaging system and said illumination system, said driving system comprising a stage supporting the object; and a signal processing system for processing image signals from said imaging system so as to detect a defect in the object, wherein said driving system comprises a first system for linearly displacing said imaging system and said illumination system relative to the object supported by the stage, and a second system for rotating said imaging system and said illumination system relative to the object supported by the stage.

12. The apparatus according to claim 11, wherein said signal processing system comprises an image processing system for processing image signals obtained at each rotation of said driving system, and a judging system for processing all results of said image processing system for a final judgment of a defect.

13. The apparatus according to claim 11, wherein the slit in said illumination system is rectangular.

14. An optical inspecting apparatus comprising:

first and second illumination systems for projecting lights of a first wavelength band and of a second wavelength band through slits to illuminate a first area and a second area on an object to be inspected, the first and second areas being separated from each other;

an imaging system for detecting an image of a third area on the surface of the object, the third area being located between the first area and the second area and not overlapping the first and second areas, said imaging system comprising a color separating member separating light in the first and second wavelength bands and linear image sensors detecting the respective light separated by said color separating member;

a driving system for displacing the object relative to said imaging system and said illumination systems, said driving system comprising a stage supporting the object; and a signal processing system for processing image signals to detect a defect in the object.

15. The apparatus according to claim 14, wherein the slits in said illumination systems are rectangular.

* * * * *